(12) United States Patent
Saikali et al.

(10) Patent No.: US 6,271,376 B1
(45) Date of Patent: Aug. 7, 2001

(54) PROCESS FOR THE PREPARATION OF N-(AMINO-4,6-DIHALO-PYRIMIDINE) FORMAMIDES

(75) Inventors: Elie Saikali, Visp; Walter Brieden, Brig-Glis, both of (CH)

(73) Assignee: Lonza AG, Basel (CH)

( * ) Notice: Subject to any disclaimer, the term of this patent is extended or adjusted under 35 U.S.C. 154(b) by 0 days.

(21) Appl. No.: 09/461,244

(22) Filed: Dec. 16, 1999

Related U.S. Application Data
(60) Provisional application No. 60/146,106, filed on Jul. 29, 1999.

(30) Foreign Application Priority Data

Dec. 21, 1998 (EP) .................................................. 98124188
Jan. 18, 1999 (EP) .................................................. 99100788
Apr. 12, 1999 (EP) .................................................. 99107161

(51) Int. Cl.[7] .......................... A61K 31/505; A61P 31/12; C07D 239/48

(52) U.S. Cl. .......................................... 544/320; 514/272

(58) Field of Search ................................................ 544/320

(56) References Cited

U.S. PATENT DOCUMENTS

| 4,965,270 | 10/1990 | Harndon et al. | 544/276 |
| 5,583,226 | * 12/1996 | Stucky et al. | 544/322 |

FOREIGN PATENT DOCUMENTS

| 0684236 | 4/1995 | (EP) . |
| 9101310 | * 2/1991 | (WO) . |

* cited by examiner

Primary Examiner—Mukund J. Shah
Assistant Examiner—Venkataraman Balasubramanian
(74) Attorney, Agent, or Firm—Fisher, Christen & Sabol

(57) ABSTRACT

A process for the preparation of N-(amino-4,6-dihalopyrimidine)formamides of the formula:

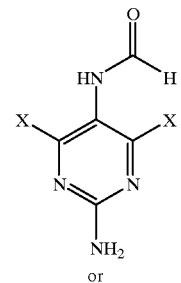

I or

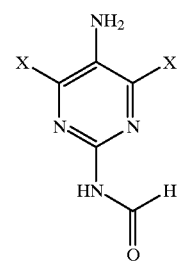

II in which X is a halogen atom, starting from 2,5-diamino-4,6-dihalopyrimidine of the formula:

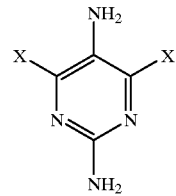

III in which X has the meaning afore-mentioned, by reaction with formic acid.

14 Claims, No Drawings

PROCESS FOR THE PREPARATION OF N-(AMINO-4,6-DIHALO-PYRIMIDINE) FORMAMIDES

This application claims benefit of U.S. Provisional application Ser. No. 60/146,106 filed on Jul. 29, 1999.

BACKGROUND OF THE INVENTION

1. Field of the Invention

The invention relates to a novel process for the preparation of N-(amino-4,6-dihalopyrimidine)-formamides of the formula

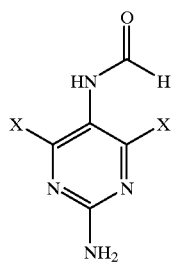

I or

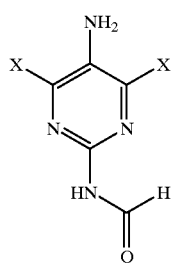

II starting from a 2,5-diamino-4,6-dihalopyrimidine of the general formula

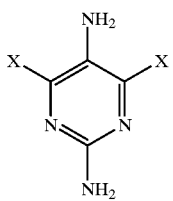

III

2. Back of the Invention

N-(Amino-4,6-dihalopyrimidine)formamides such as N-(2-amino-4,6-dihalopyrimidin-5-yl)formamide are important intermediates for the production of antiviral nucleotide derivatives (EP-A 0 684 236).

To date, a number of processes for the preparation of N-(2-amino-4,6-dihalopyrimidin-5-yl)formamide have been disclosed. Thus EP-A 0 684 236, for example, describes a process for the preparation of N-(2-amino-4,6-dihalopyrimidin-5-yl)formamide starting from an aminomalonic ester. In this process, the aminomalonic ester is first cyclized to 2,5-diamino-4,6-dihydroxypyrimidine with guanidine in the presence of an alkoxide and then 4,6-dichloro-N'-(dimethylaminomethylene)pyrimidine-2,5-diamine is formed from this with phosphorus oxychloride in the presence of dimethylformamide. The latter is subsequently converted into the desired product using aqueous propionic acid.

The disadvantages of this process are, on the one hand, the moderate yield of desired product and, on the other hand, the fact that this process proceeds via 3 stages.

To date, a number of processes for the preparation of 2,5-diamino-4,6-dihalopyrimidines such as 2,5-diamino-4,6-dichloropyrimidine have also been disclosed. For example, WO 91/01310 describes a process for the preparation of 2,5-diamino-4,6-dichloropyrimidine starting from 2,5-diamino-4,6-dihydroxypyrimidine in the presence of phosphorus oxychloride and a quaternary ammonium halide or a weakly basic tertiary amine or its salt. In this process, the phosphorus oxychloride serves as a solvent.

This process has the disadvantage that it is not reproducible on the industrial scale and the desired final product is only obtained in low yield.

BROAD DESCRIPTION OF THE INVENTION

The object of the present invention was to make available a simpler process for the preparation of N-(amino-4,6-dihalopyrimidine)formamides, in which the desired product is obtained in good yield.

Surprisingly, it has now been found that if a 2,5-diamino-4,6-dihalopyrimidine of the general formula

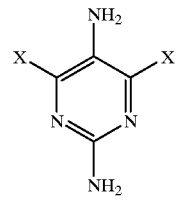

III in which X is a halogen atom is reacted with formic acid, the final products of the general formula I or II are obtained directly, i.e. without intermediates, in excellent yield.

Cl or Br can be employed as the halogen atom, preferably Cl is employed. Accordingly, 2,5-diamino-4,6-dichloro- or 2,5-diamino-4,6-dibromopyrimidine is preferably employed as the 2,5-diamino-4,6-dihalopyrimidine.

The formic acid employed below is at least 70–98% strength formic acid.

Expediently, if the preparation of the product of the formula I is desired, a 70–80% strength formic acid is employed and the reaction is carried out at a temperature of 20° C. to 60° C., preferably of 25° C. to 55° C.

If the preparation of the product of the formula II is desired, expediently an 80–98% strength formic acid is employed and the reaction is carried out at a temperature of 0° C. to 30° C., preferably of 10° to 25° C.

Surprisingly, it has also been found that the starting material 2,5-diamino-4,6-dihalopyrimidine of the general formula III is obtained in good yield if 2,5-diamino-4,6-dihydroxypyrimidine or its salt of the formula

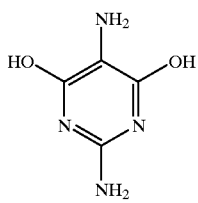

is reacted with a halogenated hydrocarbon as a solvent in the presence of a phosphorus oxyhalide and a quaternary ammonium halide or a tertiary amine.

2,5-Diamino-4,6-dihydroxypyrimidine is a commercially available compound. A suitable 2,5-diamino-4,6-dihydroxypyrimidine is also its salts such as its hydrohalide salts such as the hydrochloride salts and hydrobromide salts.

The phosphorus oxyhalide employed is expediently phosphorus oxychloride or phosphorus oxybromide.

The amine used can be a tertiary amine or its salts such as its hydrochloride or hydrobromide salts. The quaternary ammonium halide employed is expediently ammonium chloride or ammonium bromide. Customarily, the amine or the quaternary ammonium halide is employed in an excess based on the 2,5-diamino-4,6-dihydroxypyrimidine, preferably 1 to 10 mol of amine are employed based on 1 mol of 2,5-diamino-4,6-dihydroxypyrimidine.

The reaction is expediently carried out at a temperature of 20° C. up to the reflux temperature of the appropriate solvent, preferably of 100° to 120° C.

The halogenated hydrocarbons used can be halogenated aliphatic hydrocarbons. Examples of halogenated aliphatic hydrocarbons are halogenated alkanes. The halogenated alkane employed can be a halogenated propane such as 1,2,3-trichloropropane.

DETAILED DESCRIPTION OF THE INVENTION

EXAMPLE 1

Preparation of 2,5-diamino-4,6-dichloropyrimidine 2,5-Diamino-4,6-dihydroxypyrimidine hydrochloride (0.14 mol, 25 g) was filled into a dry reactor. Dry 1,2,3-trichloropropane (51.96 ml) was then added and the whole was stirred. Subsequently, tetramethylammonium chloride (0.29 mol, 31.25 g) and then $POCl_3$ (0.54–0.81 mol, 124.9–83.28 g, 50.6–75.9 ml) were added. The reaction was heated at reflux temperature (about 115° C.) for 24 h. The reaction was then cooled to below 50° C., ice water (24.44 mol, 440.44 g) was added and the whole was kept below 55° C. Subsequently, the reaction was adjusted to a pH of between 6.5 and 7.0 using 50% strength NaOH (3.12 mol, 124.92 g, 163.3 ml) and the temperature was kept below 55° C. The reaction was stirred at between 50 and 60° C. for 30 min. Tetrahydrofuran (3.7 mol, 267.0 g, 300 ml) was then added. In order to remove undesired material, the whole mixture was filtered through Celite and the filter cake was then washed with ethyl acetate (20.5 mol, 1806.58 g, 2002.86 ml) for subsequent extraction. The organic phase (tetrahydrofuran and ethyl acetate) was washed 3 times with water (5.57 mol, 100.32 g, 100.32 l), dried over $NaHCO_3$ and filtered. Ethyl acetate was removed by vacuum distillation. Hexane (0.77 mol, 66.14 g, 100.36 ml) was then added to the residual organic material, and the whole was cooled to below 10° C., filtered and then dried at 50° C. in vacuo. The title product (0.09 mol, 15.71 g) was obtained as a slightly brownish solid, corresponding to a yield of about 65% based on 2,5-diamino-4,6-dihydroxypyrimidine employed.

EXAMPLE 2

Preparation of N-(2-amino-4,6-dichloropyrimidin-5-yl)-formamide 2,5-Diamino-4,6-dichloropyrimidine (0.01 mol; 2.0 g) and water (0.25 mol; 4.55 ml) were stirred at room temperature. 98% strength formic acid (0.4 mol; 18.27 g; 14.97 ml) was then added to the reaction. The reaction was subsequently heated to 50–55° C. and kept at this temperature for 3 h.

Toluene (0.38 mol; 34.6 g; 40 ml) was then added for the azeotropic distillation under high vacuum at 50° C. (toluene was added twice to guarantee a good distillation, i.e. a total of 80 ml).

The product was subsequently filtered, washed with water and then dried at 60° C. in vacuo. 0.01 mol (2.0 g) of the abovementioned product was obtained, corresponding to a yield of about 90%.

EXAMPLE 3

Preparation of N-(5-amino-4,6-dichloropyrimidin-2-yl)-formamide

A solution of 2,5-diamino-4,6-dichloropyrimidine (0.001 mol; 2.0 g) and 98% strength formic acid (0.5 mol, 22.96 g, 18.8 ml) was stirred overnight at room temperature. Toluene (0.94 mol, 86.76 g, 18.82 ml) was then added and the reaction was cooled to 0°–5° C.

The product was filtered off and washed with water (1.11 mol, 20.0 g, 20.0 ml). The product was subsequently dried at 50° C. in vacuo. N-(5-Amino-4,6-dichloropyrimidin-2-yl)formamide was detected in the $^1H$ NMR as a single product. 0.01 mol (1.62 g) of the abovementioned product was obtained, corresponding to a yield of about 70%.

What is claimed is:

1. A process for the preparation of N-(amino-4,6-dihalopyrimidine)formamides of the formula:

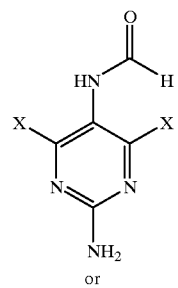

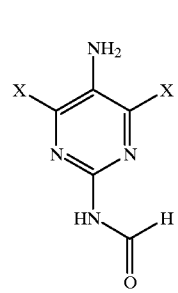

in which X is a halogen atom, comprising reacting a 2,5-diamino-4,6-dihalopyrimidine of the formula:

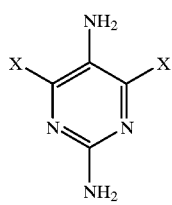

in which X has the meaning mentioned above, with formic acid of sufficient strength to produce the N-(amino-4,6-dihalopyrimidine)formamide of formula I or with formic acid of sufficient strength to produce the N-(amino-4,6-dihalopyrimidine)formamide of formula II.

2. The process according to claim 1 wherein a 70 percent up to 80 percent strength formic acid is employed for the preparation of the product of formula I and the reaction is carried out at a temperature of 20° C. to 60° C.

3. The process according to claim 1 wherein an 80 percent to 98 percent strength formic acid is employed for the preparation of the product of formula II and the reaction is carried out at a temperature of 0° to 30° C.

4. The process according to claim 2 wherein the 2,5-diamino-4,6-dihalopyrimide has formula:

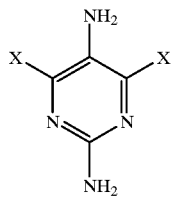

comprising reacting a 2,5-diamino-4,6-dihydroxy-pyrimidine or a salt thereof of the formula:

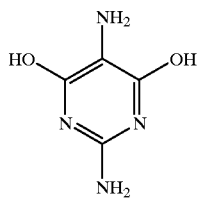

with a phosphorus oxyhalide and a quaternary ammonium halide or a tertiary amine or a salt of said amine in a halogenated hydrocarbon as a solvent.

5. The process according to claim 4 wherein the reaction is carried out at a temperature of 20° C. up to the reflux temperature of the halogenate hydrocarbon solvent.

6. The process according to claim 5 wherein the solvent employed is a halogenated alkane.

7. The process according to claim 3 wherein the 2,5-diamino-4,6-dihalopyrimidine has formula:

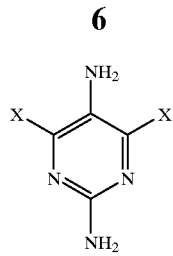

comprising reacting a 2,5-diamino-4,6-dihydroxy-pyrimidine or a salt thereof of the formula:

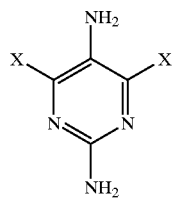

with a phosphorus oxyhalide and a quaternary ammonium halide or a tertiary amine or a salt of said amine in a halogenated hydrocarbon as a solvent.

8. The process according to claim 7 wherein the reaction is carried out at a temperature of 20° C. up to the reflux temperature of the halogenated hydrocarbon as a solvent.

9. The process according to claim 8 wherein the solvent employed is a halogenated alkane.

10. The process according to claim 2 wherein the reaction is conducted at 25° to 55° C.

11. The process according to claim 3 wherein the reaction is conducted at 10° to 25° C.

12. The process according to claim 1 wherein the 2,5-diamino-4,6-dihalopyrimidine is 2,5-diamino-4,6-dichloropyrimidine or 2,5-diamino-4,6-dibromopyrimidine.

13. The process according to claim 1 wherein the 2,5-diamino-4,6-dihalopyrimidine has formula:

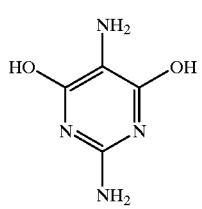

comprising reacting a 2,5-diamino-4,6-dihydroxypyrimidine or a salt thereof of the formula:

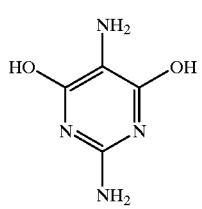

with a phosphorus oxyhalide and a quaternary ammonium halide or a tertiary amine or a salt of said amine in a halogenated hydrocarbon as a solvent.

14. The process according to claim 13 wherein the solvent is a halogenated alkane.

* * * * *